Figure 1:
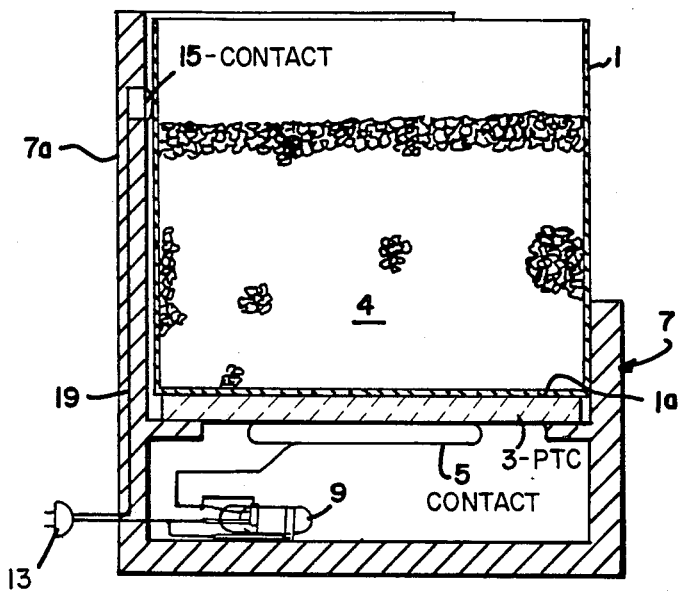
Figure 2:
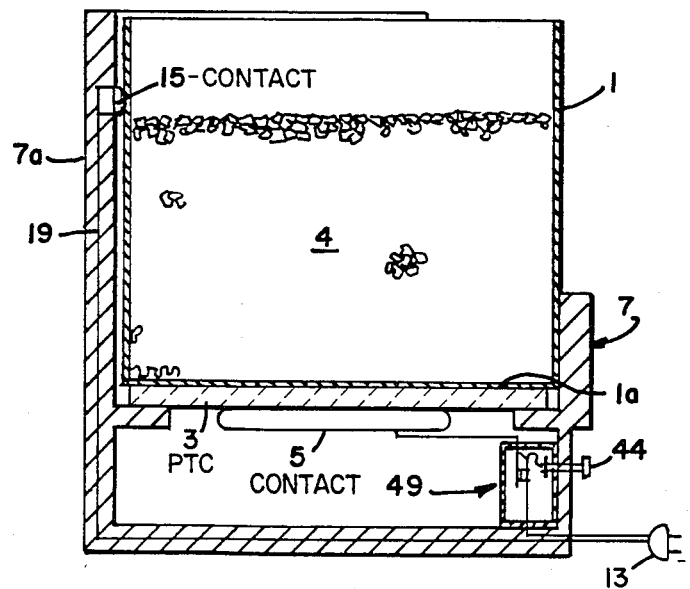
Figure 3:
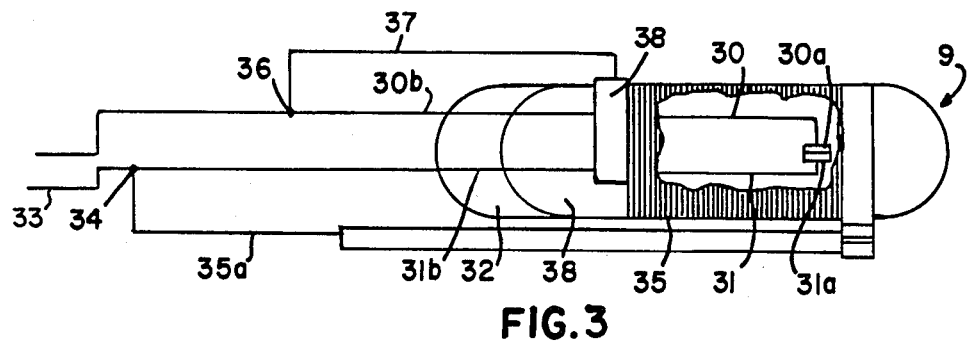
Figures 4A, 4B:
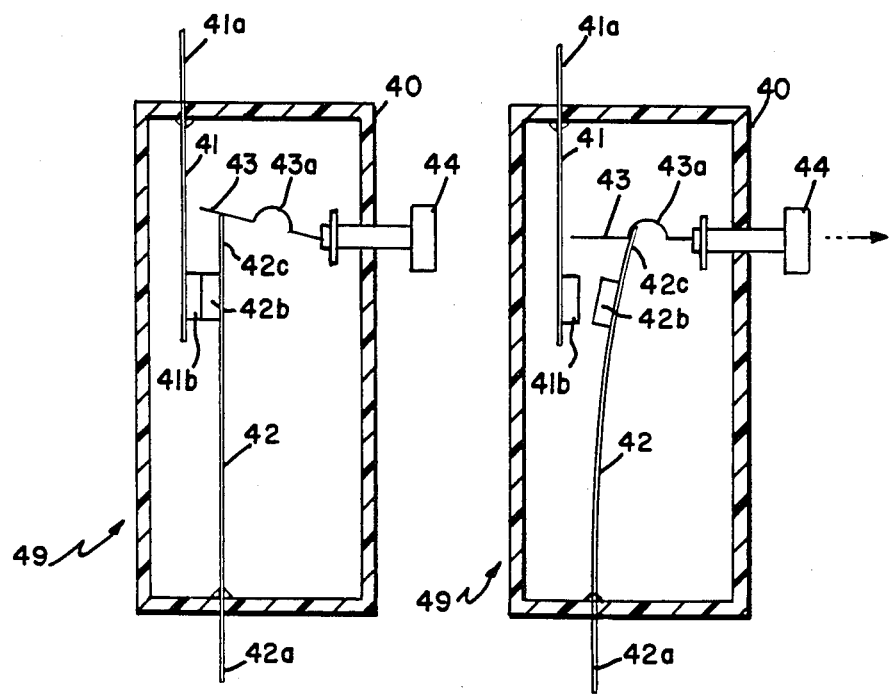

United States Patent [19]

Manchester

[11] Patent Number: 4,758,708
[45] Date of Patent: Jul. 19, 1988

[54] INSECTICIDE DISPENSER WITH TEMPERATURE SENSOR

[75] Inventor: Steven T. Manchester, Limerick, Me.

[73] Assignee: GTE Products Corporation, Stamford, Conn.

[21] Appl. No.: 892,611

[22] Filed: Aug. 4, 1986

[51] Int. Cl.$^4$ .............................................. H05B 3/14
[52] U.S. Cl. .................................. 219/272; 219/275; 219/504; 219/432; 219/433; 219/511; 422/126
[58] Field of Search ................................... 219/271–276, 219/511, 504, 505, 441, 442, 432, 433; 337/75, 91, 103; 422/305, 306, 125, 126

[56] References Cited

U.S. PATENT DOCUMENTS

| | | | |
|---|---|---|---|
| 1,830,578 | 11/1931 | Vaughan | 337/103 |
| 1,908,055 | 5/1933 | Riley | 219/275 |
| 1,908,676 | 5/1933 | Appelberg | 219/511 |
| 2,267,546 | 12/1941 | Warner | 337/91 |
| 2,426,906 | 9/1947 | Vaughan | 219/511 |
| 2,508,637 | 5/1950 | Bolesky | 337/91 |
| 2,685,020 | 7/1954 | Laibow | 219/275 |
| 3,079,485 | 2/1963 | Groves | 219/518 |
| 4,163,038 | 7/1979 | Nishimura | 219/275 |
| 4,324,974 | 4/1982 | Steiner | 219/441 |
| 4,571,485 | 2/1986 | Spector | 219/276 |

Primary Examiner—Joseph W. Hartary
Assistant Examiner—Teresa J. Walberg
Attorney, Agent, or Firm—James Theodosopoulos

[57] ABSTRACT

An insecticide dispenser capable of initiating the volatilization of a charge of insecticide to fumigate a room and then automatically shutting itself off during, or at the completion of the dispensing of the insecticide, whereby the dispenser can be safely left unattended during the fumigation of a room. The dispenser includes a container for the insecticide disposed upon a PTC heater, the elements being arranged adjacent a bimetal switching device that opens upon sensing a predetermined temperature, and can hold itself in the open position until intentionally reset. When the electrical circuit is open, the power supply to the PTC heater is broken and the heating will be discontinued.

6 Claims, 2 Drawing Sheets

INSECTICIDE DISPENSER WITH TEMPERATURE SENSOR

FIELD OF THE INVENTION

The present invention relates to electrically heated insecticide dispensers for rooms and particularly to those which are adapted to disperse a charge of insecticide from a container which is to be used only once, and in which the insecticide dispenser will shut itself off automatically when the charge has been dispensed.

SUMMARY OF THE PRIOR ART

Insecticide dispensers are well known to the art and devices have previously been introduced which are adapted to dispense insecticides into a room when a container is heated. For example, the U.S. Pat. No. 4,391,781, to van Lit, discloses a resistance heating device that can be utilized with a mat of paper that has been impregnated with an insecticide. The paper strip is urged against the resistance heater so that when the current is turned on, it will dispense the insecticide that is held on the paper. The paper is held against the resistance heating element by a clamp arm that presses the mat against the surface. A depressible lever engages the clamp arm and moves it away from the heating surface thereby releasing the paper strip to facilitate its replacement. In the van Lit patent, however, no disclosure is made of a container of insecticide and the limiting of the dispensing is controlled by the amount of vaporizable material that is held within the paper. No attempt is made in the van Lit patent to shut the resistance heating element off when the vaporizable material has been fully dispensed.

Since the present invention relates to dispensers for insecticides that utilize cannisters which are to be used only once, it is necessary to turn off the resistance heating element when the vaporizable material is fully dispersed into the room. The usual approach for dispensing such vaporizable material is to initiate the vaporization and then quickly leave the room where the dispenser has been disposed. The room is not reentered until quite a while later, when the vapor has settled and is not toxic to the person who is doing the fumigation. If the resistance heater were left on during the entire waiting period, a possibility exists that the dispenser could overheat and cause a fire while it is unattended. Thus, while the van Lit patent may be appropriate for dispensing certain small quantities of volatilizable material, 1 have found that it is inappropriate for large scale fumigation of entire rooms.

The U.S. Pat. No. 4,202,472, to Lin, discloses the use of a device for bagging trash and simultaneously dispensing insecticides or repellents. The insecticide or repellent is slowly dispensed into the trash to prevent the breeding of micro-organisms. The device does not involve the use of electrical heating for the container and dispenser and thus is not adaptable for use for fumigating a room. The U.S. Pat. No. 4,316,279, to Beacham, discloses a combined container and dispenser for dispensing a volatile product such as an air freshener or insecticide. The invention involves a continuous, low rate dispensing of the volatile product in an ambient atmosphere and is especially not related to the sudden volatilization of large quantities of insecticides such as are contemplated in the present invention. The invention of Beacham is designed to be unobtrusively stuck or hung to a hidden surface so that it is not normally observable by persons nearby whereby the vaporizable material will slowly disperse into the room where it is disposed.

Automated aerosol mist dispensers are disclosed in the U.S. Pat. No. 3,974,941 to Mettler. Patentee discloses a device for injecting short bursts of an atomized liquid such as air fresheners, medicines or insecticides at desired intervals from a spray nozzle in communication with a conventional aerosol can that contains a fluid under pressure. With Mettler's invention, an automated aerosol mist dispenser is disclosed that affords a secure interconnection between the pressurized can of fluid and the control valve mechanism and which is safe against undue leakage, even at relatively high temperatures owing to the provision of a balancing piston feature. No concept, however, is disclosed by Mettler for dispensing a large volume of insecticide into a room in a single charge through the use of a controlled resistance heating element.

U.S. Pat. Nos. 3,151,785, to Scarpa, and to Kare, No. 3,466,789, involve the use of liquid insecticide dispensers in which the rate of liquid that is being dispensed is controlled though slow dripping of the liquid and subsequent atmospheric volatilization. While Kare may disclose a single dose dispenser for the insecticide, no disclosure is made of electrically heating the dispenser to volatilize its contents.

SUMMARY OF THE INVENTION

According to the present invention, I have discovered an insecticide dispenser that can be electrically heated to dispense the insecticide and then shut itseli off automatically. The heat is radiated from a PTC heater (as will be described later) and initiates a self-sustaining, exothermic chemical reaction in the insecticide-carrier mixture that is held in an electrically conductive container. The container in which the chemical reaction occurs and the PTC heater are disposed so as to heat a snap-action bimetal switch and swing the bimetal from a cold, closed position to an open position which will turn off the PTC heater. Opening the bimetal switch occurs when the switch senses a predetermined ambient temperature. Once it has opened, the bimetal is kept opened (since it will want to close as the bimetal cools) by means of a heater that commences heating when the bimetal swings open or by means of a latching mechanism that will mechanically keep the bimetal open. In accordance with the present invention, either mechanism for maintaining the bimetal in the open condition requires an intentional intervention on the part of the user to either unlock the latch or turn off the heater. The container that holds the insecticide-carrier mixture is adapted to be part of the electrical circuit and its placement in a holder completes the circuit. When the bimetal is opened, the circuit will break, thereby discontinuing heating in the dispenser and preventing its overheating while unattended.

When the insecticide is volatilized, or during the volatilization, the bimetal will open and break the electric circuit leading to the PTC heater and the heating will be discontinued. The container in which the insecticide is disposed can be used only once, thereby preventing the possibility of injuring people through subsequent uses of it, or by using materials that are not designed for it. The utilization of the dispenser of the present invention involves a person setting up the device and then turning on the power to commence the volatilization of the insecticide. When the heating has commenced, the fumigator promptly leaves the room in which the action has been initiated and closes the door, thereby containing the insecticide within the room and allowing it to do its work. The door is not opened for a significant amount of time so as to prevent poisoning the fumigator. Since it is not desirable to continue heating the container that holds the insecticide for all of the time the fumigator is out of the room because of the possibility of overheating or fire, the dispenser of the present invention is designed to turn itself off by breaking the electrical circuit thereby turning it off and eliminating these possibilities.

My insecticide dispenser utilizes the PTC (positive temperature coefficient ceramic) heater to initiate the chemical reaction. The PTC heater heats the insecticide container to a precise temperature and maintains that temperature over a period of time sufficient to initiate the reaction and volatilize the insecticide.

PTC heaters have been in use for many years. Such heaters offer several operating advantages over conventional resistance heating elements in the heating of containers of insecticides. They generally are flat and made from doped barium titanate ceramics which have a sharp positive temperature coefficient of resistance. The PTC ceramics are designed such that below a critical temperature, the resistance of the ceramic remains at low value and is essentially constant. When a particular temperature is reached, a crystalline phase change takes place in the ceramic and this abrupt change in crystal structure is accompanied by a sharp increase in the resistance at the crystalline grain boundaries. The result of this crystalline change is an increase in the heater resistance of several orders of magnitude over a very small temperature change. A barium titanate heater with a room temperature of resistance of 3.0 ohms will increase to 1000 ohms or more during the crystalline phase change. The temperature at which the crystalline phase change takes place can be adjusted in the PTC manfacturing process through the use of appropriate chemical additives and can be varied between 60° and 180° C.

When energized with a suitable voltage by applying current to the opposite side of it, the PTC ceramic rapidly heats up to a predetermined operating temperature and then "locks in" at this temperature. This rapid warm up is due to the initial low resistance of the PTC ceramic heater which results in an internal high power input of the heater. The "lock in" is due to the abrupt increase in resistance which causes generated power to be reduced until it equals dissipated power. At this point, a thermal equilibrium is achieved and the PTC heater self regulates itself at that temperature.

Through the use of a bimetal switch that locks in an open position until a deliberate act is initiated to close it, a simple mechanism is provided for turning off the dispenser without someone being present. An inexpensive, safe way to dispense insecticides can be achieved.

DESCRIPTION OF THE DRAWINGS

FIGS. 1 and 2 are elevational views, partially in cross section, of two embodiments of an insecticide dispenser utilizing a pTC heater and adapted to turn itself off when the volatilization of the insecticide has commenced and not turn itself on again until there is an intentional act to do so. In FIG. 1, a thermally actuated bimetal switch is shown that maintains itself in an open position with an externally wrapped heater. In the embodiment shown in FIG. 2, the switch has a locking mechanism that requires a manual unlocking. FIGS. 3 and 4*a* and 4*b* are examples of the types of thermally actuated switches that can be used with the dispenser of the present invention.

DESCRIPTION OF THE PREFERRED EMBODIMENTS

In FIG. 1, an insecticide dispenser 7 with an electrically conductive container 1 is shown. The bottom wall 1*a* is disposed upon a PTC heater 3. The PTC heater 3 rests on, and is in electrically connected to contact 5. An exposed contact member 15 is disposed upon the inside of a side wall *7a* and is arranged to form an electrical connection with the electrically conductive container 1 to complete the circuit with the PTC heater 3.

When turned on, the PTC heater 3 will initiate a chemical reaction within a mass of insecticide 4 held within the container 1. The mass of insecticide contains a mixture of the active ingredient (the insecticide) dispersed within a carrier. When the heating commences in the container 1, a chemical reaction begins and copious volumes of smoke are given off. The chemical reaction is self-sustaining, that is additional heat need not be used once the reaction has commenced. The reaction will continue until all of the carrier has reacted and the insecticide has been volatilized.

The heat from the chemical reaction in the container and the PTC heater 3 will radiate upon the temperature sensing device 9 that is disposed in the dispenser 7 and eventually will open the bimetal to break the circuit. When the electrical circuit to the PTC is broken, the PTC heater 3 will cease heating the container 1, but the self-sustaining exothermic reaction will continue to volatilize the insecticide. The thermally responsive switch is disposed within the dispenser 7 and adjacent the PTC heater 3 so that when a predetermined temperature is reached for a sufficient time to initiate the chemical reaction within the container 1, the PTC heater 3 will shut off. In this way, as the insecticide is volatilizing, or when the insecticide has been fully volatilized from the container 1, no additional heat will be applied, thereby preventing damage to the dispenser and possibly preventing a fire.

The dispenser 7 shown in FIG. 1 utilizes a bimetal switch 9 that is interposed in the line between the electrical contact 5 and the plug 13. An example of the thermally responsive switch that 1 use in this embodiment is shown in FIG. 3 and includes a movable bimetal member 30 with an electrical contact 30*a*, and a rigid member 31 which supports an electrical contact 31*a*. A lead-in wire 31*b*, connected to member 31, extends through a glass seal 32 to the outside of the switch 9. A lead-in wire 30*b* connected to member 30, also extends through the glass seal 32 to the outside. Lead-in wire 33 is attached at a junction 34 to a heater wire 35*a* which in turn is connected to heater 35 that is wrapped around the outside of the glass envelope 38 that seals the switch 9. The other end of the heater 35 is attached to lead-in wire 30*b* at junction 36. In operation, current will normally flow through lead-in wire 30*b* and the bimetal 30, through electrical contacts 30*a* and 31*a* and then through rigid member 31 to return to the outside of the glass seal 32 through lead-in wire 31*b*. When bimetal member 30 swings open, thereby disconnecting the connection between electrical contacts 30*a* and 31*a*, due to the relative resistances, current will commence flowing through connecting wire 37 to heater wire 35.

Heater wire 35 will commence heating the glass envelope 38 that surrounds the bimetal switch and will radiate its heat inwardly towards the bimetal switch to keep it open so long as current is flowing therethrough. When the current flow is disconnected, as would be the case if the fumigator were to reenter the room at the conclusion of a fumigation operation and unplug the dispenser, the heater would immediately cool down and bimetal element 30 would swing back into contact with the rest of the circuit at electrical contacts 30a and 31a. A new container of insecticide can then be placed in the insecticide dispenser housing 7 and fumigation can be recommenced.

In the preferred embodiment, the thermally responsive switching device is disposed at a sufficient distance from the PTC heater 3 to open after a time delay which is adequate to start the chemical reaction within the container 1 of insecticide. This distance can be varied, depending upon the temperature which opens the bimetal, the desired temperature which must be achieved within the PTC to initiate the chemical reaction and other factors such as the mass of the insecticide dispenser housing. When the bimetal swings open and the heat is initiated around the thermally responsive switch, the bimetal will stay open until the entire circuit is disconnected, thereby providing a safety factor which can provide significant benefits to the user of the equipment. For example, a thermally responsive bimetal switch which snaps open at 120° C. and is located less than about one inch from the PTC will provide a sufficient delay to the insecticide dispenser to initiate the chemical reaction and volatilize the insecticide that is in the container 1.

In FIG. 2 of the drawings, an insecticide dispenser similar to that shown in FIG. 1 is illustrated. In this embodiment, however, the thermally responsive bimetal switch element with a heater wrapped around it has been replaced with a single throw action bimetal switch with a locking mechanism such as shown in FIGS. 4*a* and 4*b* of the drawing.

In the device shown in FIGS. 4*a* and 4*b*, a rigid member 41 is disposed with a lead-in wire 41*a* extending though the side wall of a housing 40. A electrical contact member 41*b* is disposed at the inward end of the support member 41 and is in a face to face relationship with a similar electrical contact 42*b* that is disposed at the inward end of a bimetal switch 42 that has a lead-in wire 42*a* extending through the side wall of the housing 40. A latch 42*c* extends beyond the electrical contact member 42*b* to engage a strike 43. Catch 43 is urged against the latch 42*c* and is arranged to move when the bimetal 42 retracts from its closed position. When bimetal 42 retracts from its closed position, latch 42*c* engages the catch 43*a* to releasable retain the bimetal 42 in the open position.

An end of strike 43 and catch 43*a* is seated in a handle 44 which can move outwardly, and when so moved, will release the latch 42*c* from the catch 43*a*. In some cases, it may be desirable to allow handle 44 pivot somewhat to allow for an easier release of latch 42*c* from catch 43*a*. In practice, when the bimetal is heated due to the PTC heater 3, the latch 42*c* will enter into catch 43*a* and will remain there temporarily until the fumigator desires to reengage the circuit. The pTC heater 3 will cool down when the current is turned off, but the bimetal will not close since latch 42*c* is seated in the catch 43*a*. When the fumigator decides to initiate another fumigation operation, the handle 44 is pulled outwardly, thereby disengaging the latch 42*c* from the catch 43*a* and allowing the bimetal to swing (with its electrical contact 42*b*), towards electrical toward electrical contact 41*b* and reengage it. When so reengaged, the circuit can be reestablished and another fumigation operation can be initiated.

Many different bimetals with many different opening temperatures between about 80° to 200° C. can be utilized in accordance with the present invention. PTC heaters having anomaly temperatures less than about 240° C. are extremely useful in initiating the chemical reactions of the present invention.

In the practice of the present invention, it is apparent that modifications and changes may be made by those with ordinary skill in the art, but it is my intention, however, only to be limited by the scope of the appended claims.

As my invention I claim:

1. An insecticide dispenser for a room, said dispenser comprising:

a housing and an electrically conductive, non-reuseable container disposed in said housing, said container being disposed upon a PTC heater, said container being adapted to receive a charge of an insecticide dispersed within a carrier, said charge requiring the application of heat to initiate a chemical reaction which produces a volatilization of the insecticide; and a first means connecting said container to one side of power supply; and a second means connecting said PTC heater to an other side of said power supply whereby when said container is placed upon said PTC heater, a circuit is formed, and heating of the container will be initiated by said PTC heater; and temperature sensing means disposed adjacent to said PTC heater, thereby to disconnect said PTC heater from said circuit when a predetermined temperature is reached, said temperature sensing means being a bimetal switch designed to snap from a closed position when cold to an open position upon sensing heat at a predetermined temperature, said sensing means being arranged to stay in said open position even if the sensed temperature falls below said predetermiend temperature.

2. The dispenser according to claim 1 wherein said bimetal is wrapped with heater means disposed in a heating relationship therewith, said heater being arranged to become actuated when said bimetal opens, and remain actuated until the circuit is broken, whereby the circuit to said PTC heater will be broken until said heater is turned off at which time said bimetal will snap closed and reset itself for another heating cycle.

3. The dispenser according to claim 1 wherein the temperature sensing means is a resetable bimetal switch, said bimetal arranged to move from a closed position when cold to an open position upon being heated to a predetermined temperature and to latch into said open position with a manually resetable latch, whereby said latch can be opened to reset said bimetal for another heating cycle of said PTC heater.

4. An insecticide dispenser for a room, said dispenser comprising:

a housing and an electrically conductive, non-reuseable container disposed in said hosuing, said container being disposed upon a PTC heater, said container being adapted to receive a charge of an insecticide dispersed within a carrier, said charge requiring the application of heat to initiate a self-sustaining, exothermic chemical reaction which produces a volatilization of the insecticide;

a first means connecting said container to one side of a power supply;

a second means connecting said PTC heater to an other side of said power supply, whereby when said container is placed upon said PTC heater, a circuit is formed, and said PTC heater will heat; and temperature sensing means disposed adjacent to said PTC heater, thereby to disconnect said PTC heater from said circuit when a predetermined temperature is reached, said temperature sensing means being disposed at a predetermined distance from said PTC heater so as to open after a delay which is sufficient to initiate said self-sustaining, exothermic chemical reaction of said insecticide and carrier in said container, said temperature sensing means being a bimetal switch designed to snap from a closed position when cold to an open position upon sensing heat at a predetermined temperature, said sensing means being arranged to stay in said open position even if the sensed temperature falls below said predetermined temperature.

5. The dispenser according to claim 4 wherein said bimetal is wrapped with heater means disposed in a heating relationship therewith, said heater being arranged to become actuated when said bimetal opens, and remain actuated until the circuit is broken, whereby the circuit to said PTC heater will be broken until said heater is turned off at which time said bimetal will snap closed and reset itself for another heating cycle.

6. The dispenser according to claim 4 wherein the temperature sensing means is a resetable bimetal switch, said bimetal arranged to move from a closed position when cold to an open position upon being heated to a predetermined temperature and to latch into said open position with manually resetable latch, whereby said latch can be opened to reset said bimetal for another heating cycle of said PTC heater.

* * * * *